(12) United States Patent
Zihlmann et al.

(10) Patent No.: US 9,138,540 B2
(45) Date of Patent: *Sep. 22, 2015

(54) AMPOULE WITH A SEAL IN TWO COMPRESSION STATES

(71) Applicant: Roche Diagnostics International AG, Rotkreuz (CH)

(72) Inventors: Ruedi Zihlmann, Langnau in Emmental (CH); Ronny-Patric Horisberger, Kirchberg (CH); Daniel Fehlmann, Rothrist (CH)

(73) Assignee: Roche Diagnostics International AG, Steinhausen (CH)

( * ) Notice: Subject to any disclaimer, the term of this patent is extended or adjusted under 35 U.S.C. 154(b) by 142 days.

This patent is subject to a terminal disclaimer.

(21) Appl. No.: 13/783,500

(22) Filed: Mar. 4, 2013

(65) Prior Publication Data

US 2013/0158486 A1 Jun. 20, 2013

Related U.S. Application Data

(63) Continuation of application No. 13/467,372, filed on May 9, 2012, now Pat. No. 8,409,150, which is a
(Continued)

(30) Foreign Application Priority Data

Sep. 1, 2007 (EP) .................................... 07017173

(51) Int. Cl.
*A61M 5/00* (2006.01)
*A61M 5/315* (2006.01)
(Continued)

(52) U.S. Cl.
CPC .............. *A61M 5/31501* (2013.01); *A61L 2/06* (2013.01); *A61L 2/07* (2013.01); *A61L 2/08* (2013.01);
(Continued)

(58) Field of Classification Search
CPC ........... A61M 2005/3123; A61M 2005/31506; A61M 2005/31508; A61M 5/19; A61M 5/3129; A61M 5/31501

USPC ......... 604/191, 207–210, 218–222, 227, 228, 604/232

See application file for complete search history.

(56) References Cited

U.S. PATENT DOCUMENTS

| 3,016,896 A | 1/1960 | Sickle |
| 4,212,309 A | 7/1980 | Moorehead |

(Continued)

FOREIGN PATENT DOCUMENTS

| EP | 0 248 210 A1 | 4/1987 |
| EP | 0 985 419 A1 | 8/1999 |

(Continued)

OTHER PUBLICATIONS

International Search Report, Appl. No. PCT/EP2008/007116, dated Dec. 12, 2008 (3 pages).

*Primary Examiner* — Aarti B Berdichevsky
(74) *Attorney, Agent, or Firm* — Dinsmore & Shohl LLP

(57) ABSTRACT

Ampoules for dispensing flowable substances and metering systems incorporating the same are described herein. An ampoule for a flowable substance includes an ampoule body comprising an interior space for receiving the flowable substance and an inner circumferential surface having a guide region and a sealing region. A piston may be disposed in the interior space of the ampoule body such that the piston is slidably displaceable along a direction of displacement. The piston includes at least one sealing element for forming a seal with the inner circumferential surface in a contact zone on the outer circumference of the sealing element. The sealing element has a first compression state when the contact zone is in the guide region and a second compression state when the contact zone is in the sealing region. A second blocking device prevents movement of the contact zone from the sealing region to the guide region.

17 Claims, 11 Drawing Sheets

Related U.S. Application Data continuation of application No. 12/713,812, filed on Feb. 26, 2010, now Pat. No. 8,197,451, which is a continuation of application No. PCT/EP2008/007116, filed on Aug. 30, 2008.

(51) Int. Cl.

| | | |
|---|---|---|
| *A61L 2/06* | (2006.01) | |
| *A61L 2/07* | (2006.01) | |
| *A61L 2/08* | (2006.01) | |
| *A61L 2/20* | (2006.01) | |
| *A61M 5/14* | (2006.01) | |
| *A61M 5/19* | (2006.01) | |
| *A61M 5/31* | (2006.01) | |

(52) U.S. Cl.
CPC . *A61L 2/081* (2013.01); *A61L 2/20* (2013.01); *A61L 2/204* (2013.01); *A61L 2/206* (2013.01); *A61M 5/1408* (2013.01); *A61M 5/19* (2013.01); *A61M 5/315* (2013.01); *A61M 5/3129* (2013.01); *A61M 2005/3123* (2013.01); *A61M 2005/31506* (2013.01); *A61M 2005/31508* (2013.01)

(56) References Cited

U.S. PATENT DOCUMENTS

| | | | |
|---|---|---|---|
| 4,755,169 | A | 7/1988 | Sarnoff et al. |
| 5,009,645 | A | 4/1991 | Silver et al. |
| 7,713,245 | B2 * | 5/2010 | Cipoletti et al. ............... 604/218 |
| 8,197,451 | B2 * | 6/2012 | Zihlmann et al. ............. 604/220 |
| 8,409,150 | B2 * | 4/2013 | Zihlmann et al. ............. 604/220 |
| 2003/0040713 | A1 | 2/2003 | Wang et al. |
| 2003/0097096 | A1 | 5/2003 | Niedospial, Jr. |
| 2007/0100293 | A1 | 5/2007 | Cipoletti et al. |

FOREIGN PATENT DOCUMENTS

| | | |
|---|---|---|
| WO | 00 71185 A2 | 11/2000 |
| WO | 01 60434 A1 | 8/2001 |

* cited by examiner

AMPOULE WITH A SEAL IN TWO COMPRESSION STATES

CROSS REFERENCE TO RELATED APPLICATIONS

This application is a continuation of U.S. patent application Ser. No. 13/467,372 filed May 9, 2012, which is a continuation of U.S. patent application Ser. No. 12/713,812 filed Feb. 26, 2010, now U.S. Pat. No. 8,197,451, which is a continuation of International Application No. PCT/EP2008/007116 filed Aug. 30, 2008, now publication no. WO 2009/027104 A1, which claims priority to European Patent application EP 07 017 173.1 filed Sep. 1, 2007.

TECHNICAL FIELD

The present specification relates to ampoules for flowable substances, and in particular, to ampoules for medically active liquids for administration with an infusion or injection device, and to metering systems with ampoules as described herein.

BACKGROUND

WO 2000/71185 A1 discloses a medicament ampoule with a plastic ampoule body in which a piston is initially held by the ampoule body with a clearance fit. After the piston and the interior space of the ampoule have been sterilized, the piston is displaced into an adjacent region of the interior space of the ampoule body where the piston together with the ampoule body forms a seal. The seal is broken by returning the piston to its initial position.

Infusion pumps based on the syringe pump principle are used for numerous medical applications to continuously supply medicaments at a constant or temporally variable rate. One example thereof is the treatment of diabetes mellitus by the continuous subcutaneous infusion of insulin. Miniaturized infusion pumps which operate according to the syringe principle have been developed for this purpose. One such pump is known, for example, from EP 985419 B1.

WO 0160434 A1 discloses a piston for use in ampoules for infusion pumps of this type. The piston has a basic body and a sealing element bonded to the basic body such as by glue, adhesive, welding, etc. In this case, the basic body is composed, for example, of a thermoplastic material such as polypropylene and the sealing element is composed of a thermoplastic elastomer such as Santoprene.

However, because of their specific properties, stoppers with sealing elements made of thermoplastic elastomers may not remain sealed for the entire required storage period of several years under changing climate conditions because they are permanently deformed under the pressure acting on them from the ampoule body. Furthermore, when an ampoule with a pressed-in stopper is stored for a relatively long period of time at a high storage temperature, a slow deformation of the ampoule body under the pressure acting on it from the stopper (i.e., creep) generally occurs, which also has a disadvantageous effect on the seal.

Embodiments described herein provide an ampoule for a flowable substance that overcomes these disadvantages.

SUMMARY

In one embodiment, an ampoule for a flowable substance is disclosed. The ampoule includes an ampoule body having an interior space for receiving the flowable substance and an inner circumferential surface having a guide region and a sealing region. The guide region and the sealing region are positioned along a longitudinal axis of the ampoule body. A piston may be disposed in the interior space of the ampoule body such that the piston is slidably displaceable along the longitudinal axis of the ampoule body in a direction of displacement. The piston may include at least one sealing element for forming a seal with the inner circumferential surface of the ampoule body in a contact zone on an outer circumference of the at least one sealing element. The ampoule also includes a second blocking device which prevents movement of the contact zone from the sealing region to the guide region. The at least one sealing element has a first compression state when the contact zone is in the guide region of the inner circumferential surface. The at least one sealing element also has a second compression state when the contact zone is in the sealing region such that the inner circumferential surface forms a fluidic seal with the at least one sealing element. When the at least one sealing element is in the second compression state, the at least one sealing element has a greater degree of compression than when the at least one sealing element is in the first compression state. The interior space of the ampoule body can have a cross section which deviates from circularity in a direction perpendicular to the direction of displacement and along the longitudinal axis of the ampoule body In another embodiment, a metering system for a flowable substance is disclosed. The metering system comprises an injection or diffusion device for dispensing the flowable substance from an ampoule having an ampoule body, a piston and a second blocking device. The ampoule body can have a cross section which deviates from a circular shape. The ampoule body includes an interior space for receiving the flowable substance and an inner circumferential surface having a guide region and a sealing region. The guide region and the sealing region are positioned along a longitudinal axis of the ampoule body. The inner circumferential surface can taper in from the guide region to the sealing region. The piston is disposed in the interior space of the ampoule body such that the piston is slidably displaceable along a longitudinal axis of the ampoule body in a direction of displacement. The piston includes at least one sealing element for forming a seal with the inner circumferential surface of the ampoule body in a contact zone on an outer circumference of the at least one sealing element. The at least one sealing element has a first compression state when the contact zone is in the guide region of the inner circumferential surface. The at least one sealing element also has a second compression state when the contact zone is in the sealing region such that the inner circumferential surface forms a fluidic seal with the at least one sealing element when the at least one sealing element is in the second compression state. The second blocking device prevents movement of the contact zone from the sealing region to the guide region. The injection or diffusion device is connectable to the piston of the ampoule to advance the piston in the interior space in the direction of displacement such that the flowable substance is dispensed from the ampoule.

DETAILED DESCRIPTION

Figure 1:
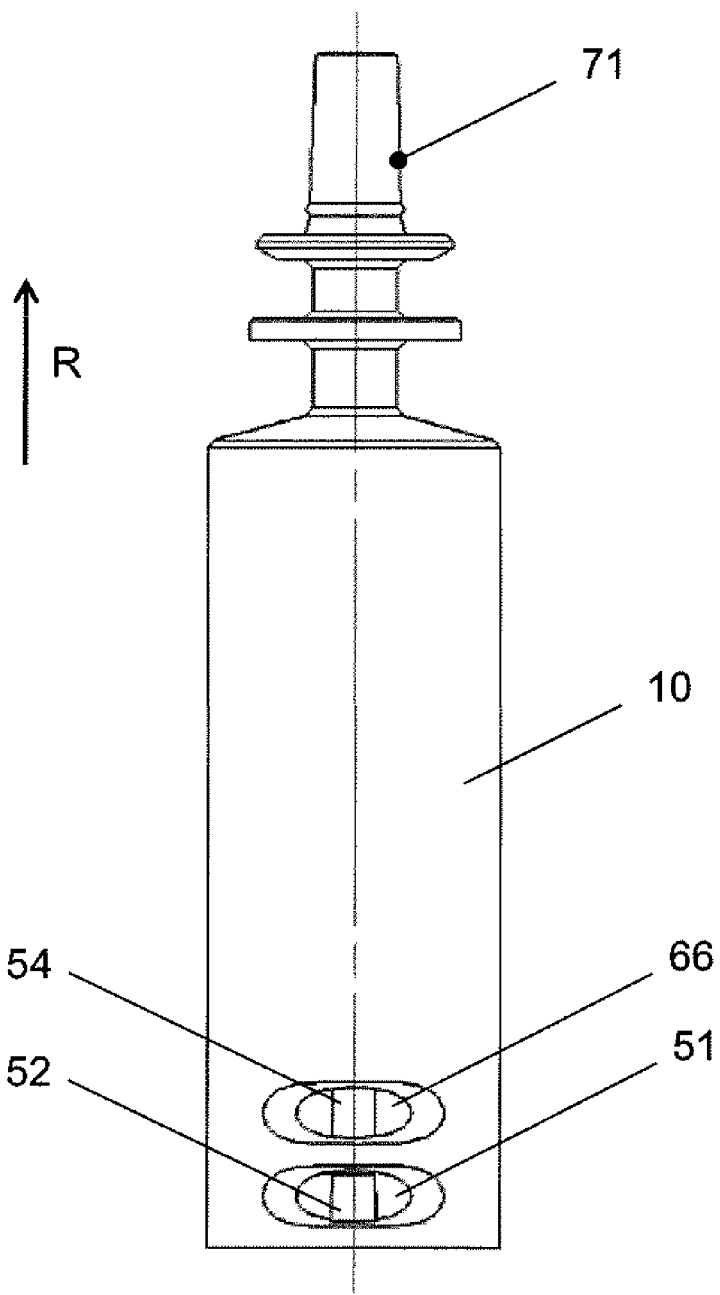
FIG. 1 depicts an ampoule according to one or more embodiments shown and described herein.

According to one embodiment, an ampoule has an ampoule body, the interior space of which receives the flowable substance. Said substance may be, for example, a low-viscosity liquid such as insulin or another medically active liquid, a high-viscosity liquid or else a pulverulent substance. The material used for the ampoule body is preferably glass or a thermoplastic, but the ampoule body may also be formed from another suitable material such as stainless steel or ceramic materials.

The ampoule may comprise a piston which has at least one sealing element that can be displaced along a direction of displacement in the interior space of the ampoule body. The direction of displacement corresponds to the direction of movement of the piston in order to empty the substance from the interior space of the ampoule body. In one embodiment, the direction of displacement corresponds to the longitudinal axis of the ampoule body. In at least one contact zone which encircles the outer circumference of the at least one sealing element, the piston makes contact with the inner circumferential surface of the ampoule body such that the piston is compressed thereby. The piston can be manufactured, for example, from a thermoplastic elastomer or a pure elastomer.

In one embodiment, the piston comprises a basic body made of a different material than the sealing element. For example, the basic body may be manufactured from a thermoplastic material of high rigidity, such as polypropylene, and the sealing element may be manufactured from a thermoplastic elastomer or pure elastomer of low Shore hardness such as Santoprene. With this construction, a high degree of rigidity (which is advantageous for the piston) can be associated with a high degree of elasticity for the sealing element. The sealing element can be formed, for example, by means of an O-ring and can be fitted into a corresponding groove in the basic body. Alternatively, two or more O-rings can be used. In one embodiment, the basic body and sealing element are bonded together such as with an adhesive, welding, glue, etc. Alternatively, the basic body and sealing element are formed as a two component injection-molded part. In further embodiments, the basic body and the sealing element are connected with a snap-in connection.

The inner circumferential surface of the ampoule body has a guide region and a sealing region along the direction of displacement. Specifically, the cross section of the interior space of the ampoule body is formed with the guide region in a plane transverse to the direction of displacement such that the at least one sealing element has a first compression state when the contact zone is in the guide region. The cross section of the interior space of the ampoule body is also formed with the sealing region such that the at least one sealing element has a second compression state when the contact zone is in the sealing region. When the sealing element is in the second compression state the sealing element has a greater degree of compression than when the sealing element is in the first compression state. In the second compression state, the inner circumferential surface of the ampoule body forms a fluidic seal together with the sealing element. The guide region may be formed such that the inner circumferential surface does not compress the sealing element or only compresses it to such a slight extent that the sealing element is not plastically compressed when the contact zone is in the guide region. (In contrast to an elastic deformation, a plastic deformation is permanently maintained even after the end of an application of force).

A measure of the deformation of the sealing element is its degree of compression which indicates the percentage of compression of the sealing element with respect to its load-free extent. When thermoplastic elastomers are used for the sealing element, said elastomers should not be compressed to more than 25% in the sealing region. In one embodiment an ampoule with a circular cylindrical cross section has an inside diameter in the sealing region of 6.5 mm and the load-free diameter of the sealing element is 6.9 mm. This results in a reduction in the diameter of the sealing element by 6.9 mm−6.5 mm=0.4 mm due to compression, which, in this example, is 5.8%.

In one embodiment, a second blocking device is provided which prevents displacement of the contact zone out of the region of the second compression state of the sealing element opposite the initial direction of displacement. In this embodiment, once the contact zone between the sealing element and the inner circumferential surface of the ampoule body has been displaced from the guide region into the sealing region thereby forming a fluidic seal, the second blocking device prevents the seal from being broken by preventing the sealing element from being withdrawn from the sealing region.

The second blocking device can comprise at least one piston-side stop, a sliding surface and a second ampoule-body-side stop.

In one embodiment, the inner circumferential surface of the ampoule body together with the at least one sealing element does not form a seal with regard to a medium with a sterilizing effect and/or radiation with a sterilizing effect when the at least one sealing element is in the first compression state. Accordingly, a medium with a sterilizing effect and/or radiation with a sterilizing effect can penetrate the interior space of the ampoule body when the at least one sealing element is in the first compression state in order to sterilize the interior space of the ampoule body.

The ampoule body may have a transition region which connects the interior space of the ampoule body in the guide region to the interior space of the ampoule body in the sealing region in a continuous manner, i.e. without jumps or edges.

Furthermore, for sealing reasons and in order to improve the guidance of the piston in the ampoule body, the sealing element and inner circumferential surface of the ampoule body can be formed in such a manner that, together with the inner circumferential surface of the ampoule body, the sealing element includes two or more contact zones and/or two or more sealing elements can be provided.

In one embodiment, the piston comprises at least one guide element which is offset relative to the at least one sealing element in the direction of an opening of the ampoule body. In this embodiment, the guide element makes contact with the inner circumferential surface of the ampoule body. This offset guide element prevents both tilting of the piston and inadvertent displacement of the piston in the ampoule body.

An ampoule according to the embodiments described herein may have a drawing-up device for displacing the piston opposite the direction of displacement. The drawing-up device may be used when filling the ampoule, to pull back the piston after the piston has been pushed all the way into the ampoule. In one embodiment, the drawing-up device is a piston rod integrally formed with the piston itself. In another embodiment, the drawing-up device is in the form of a piston rod that can be releasably coupled to the piston.

In order to ensure a smooth movement of the piston in the interior space of the ampoule body and low frictional forces, the ampoules of the embodiments described herein may include a viscous lubricant, such as silicone oil, which forms a lubricating film on the inner circumferential surface of the ampoule body. As an alternative or in addition, the friction can also be reduced by other measures. For example, the inner circumferential surface of the ampoule body and/or of the sealing element may be coated with a layer of silicone or Teflon.

The piston of an ampoule according to the embodiments described herein may comprise a coupling device for coupling the piston to an advancing unit of an injection or infusion device. In this case, the coupling device comprises a plane surface to which a compressive force can be applied by a pressure plate of the advancing unit. In another embodiment, the coupling device comprises an external thread or a rack which can be engaged with a lock nut or a gear wheel of an advancing unit.

The ampoule body may be provided with at least one outlet opening which is used both for filling the ampoule and for emptying the ampoule. In one embodiment, the at least one outlet opening is arranged coaxially with respect to an axis of symmetry of the ampoule body.

In a further embodiment, an outlet opening is arranged transversely with respect to the direction of displacement. In one embodiment, the outlet opening leads into a Luer cone. In another further embodiment, the outlet opening is closed by means of a septum which can be pierced by a hollow cannula in order to vent, fill and empty the interior space of the ampoule.

When the contact zone is located between the inner circumferential surface of the ampoule and the sealing element in the guide region, slight compression of the sealing element indicates that the piston fits loosely in the ampoule body. In order to prevent an inadvertent removal of the piston from the ampoule body in this state, a first blocking device may be provided. The blocking device prevents withdrawal of the contact zone from the region of the first compression state of the sealing element opposite the direction of displacement.

The first blocking device can comprise at least one piston-side stop, a sliding surface and a first ampoule-body-side stop.

When an ampoule has a first blocking device, the first and the second blocking devices may be similar in design to each other. In particular, the at least one piston-side stop of the first blocking device may be the at least one piston-side stop of the second blocking device. In addition, the at least one sliding surface of the first blocking device may be the at least one sliding surface of the second blocking device.

A piston-side stop which is utilized in conjunction with both the first blocking device and the second blocking device and a sliding surface which is common to a first blocking device and a second blocking device may be designed as a catch which is arranged on a radially resilient spring arm surrounding the piston and extending in a direction towards an open end side of the ampoule body. In this embodiment, the wall of the ampoule body has at least one first cutout and at least one second cutout which is offset in the direction of displacement R with respect to the first cutout, with the first ampoule-body-side stop being formed by the wall of the at least one first cutout and the second ampoule-body-side stop being formed by the wall of the at least one second cutout. In the unloaded state of the spring arm, the at least one catch can project into the at least one first cutout and, alternatively, into the at least one second cutout.

Furthermore, the at least one spring arm can be designed in such a manner that the inner circumferential surface of the ampoule body can be deformed such that the at least one catch presses resiliently against the inner circumferential surface of the ampoule. This can improve the guidance of the piston in the interior space of the ampoule body and, because of the pressure, can counteract an inadvertent displacement of the piston.

The interior space of the ampoule body can have different cross-sectional shapes perpendicular to the direction of displacement of the piston; in one embodiment, the cross-sectional shape is circular. In other embodiments, the ampoule body has a cross section which deviates from the circular shape; in particular, in one embodiment, it has an elliptical shape. In a further embodiment, the interior space of the ampoule body has at least one pair of mutually opposite, parallel boundary surfaces. The latter can be connected via curved, for example semi-cylindrical, circumferential surfaces. An ampoule-body shape which deviates from the cylindrical shape may be particularly advantageous for use in injection or infusion systems.

An ampoule according to the embodiments described herein may be provided in sterile packaging, with the at least one sealing element being in the first compression state. In this case, removal of the piston from the ampoule body may be prevented by means of a first blocking device. Before the ampoule is filled, the piston is displaced in the direction of displacement, as a result of which the contact zone between the at least one sealing element and the inner circumferential surface of the ampoule is displaced from the guide region via the transition region into the sealing region, with the at least one sealing element being transferred into the second compression state. Further movement of the piston in the direction of displacement vents the interior space of the ampoule. At the same time, a viscous lubricant present in the interior space of the ampoule body may be distributed uniformly over the inner circumferential surface of the ampoule body by movement of the piston. If the at least one outlet opening is closed by a septum, the latter is pierced by a hollow cannula before the movement of the piston.

Venting of the interior space is followed by filling the interior space with the active substance liquid. The filling preferably taking place through the at least one outlet opening, which in this case, is used as a filling opening. If the at least one outlet opening is closed by a septum, the latter is pierced with a hollow cannula (which has already been used for the venting) or with a further hollow cannula. Filling is performed by pulling the piston opposite the direction of displacement with the aid of the drawing-up device, which produces a negative pressure between the outlet opening and piston in the previously vented interior space of the ampoule body. The negative pressure causes the active substance liquid to be sucked into the interior space of the ampoule body. As an alternative, it may also be possible to press the active substance liquid by means of positive pressure through the outlet opening into the interior space of the ampoule body, with the active substance liquid displacing the piston opposite the direction of displacement.

The embodiments described herein also relate to ampoules for a flowable substance which comprise at least one first partial ampoule according to embodiments described herein and a second partial ampoule according to the embodiments described herein. This facilitates an overall flat design of an ampoule having a relatively large capacity and a small internal cross section with improved rigidity. In some embodiments, the partial ampoules are identical and, in particular, have an identical interior space. However, depending on the space conditions, for example in an injection or infusion device, the individual ampoules may also have different cross sections. The partial ampoules may be arranged with respect to each other in such a manner that they have a common direction of displacement. In this case, the pistons of the partial ampoules may be connected to each other with a connecting piece integrally formed with the pistons such as when the connection piece and pistons are injection-molded. However, in other embodiments, the directions of displacement may also be at an angle with respect to each other. In particular, the individual ampoules may also be arranged with respect to each other in such a manner that their directions of displacement are opposed to each other. The at least two partial ampoules preferably have a common outlet opening. However, a plurality of outlet openings, for example one outlet opening per partial ampoule, may also be provided.

Embodiments described herein also relate to metering systems for a flowable substance, in particular for the infusion of insulin or other medically active substances. Such a system comprises an ampoule according to the embodiments described herein and an injection or infusion device which is operatively coupled to the ampoule. In particular, the injection or infusion device can fully or partially accommodate the ampoule.

Furthermore, the metering system may comprise an adapter which can be releasably coupled to the injection or infusion device, and an injection or infusion cannula, with the adapter coupling the outlet opening of the ampoule fluidically to the injection or infusion cannula and forming a stop for securing the ampoule in the direction of displacement. In this case, the injection or infusion cannula can be coupled such that it directly adjoins the adapter or can be coupled to the adapter via a catheter. In one embodiment, the outlet opening of the ampoule comprises a septum which is pierced by a cannula surrounded by the adapter.

The adapter may be coupled to the injection or infusion device by relative movement between adapter and injection or infusion device transversely with respect to the direction of displacement, with the relative movement at the same time fluidically coupling the outlet opening of the ampoule to the adapter.

The adapter can furthermore have a monitoring device for monitoring the metering, for example in the form of a pressure sensor, a pressure switch or a flow sensor.

The injection or infusion device preferably comprises an advancing unit for the controlled displacement of the piston in the direction of displacement.

In particular, the advancing unit can comprise a piston rod which can retract into the ampoule through an ampoule opening facing the advancing unit, and can thus displace the piston in a controlled manner within the ampoule. As an alternative, the piston may also comprise a threaded rod or a rack which can be in engagement with a lock nut surrounded by the advancing unit, or with a toothed wheel.

The embodiments described herein may be explained with reference to exemplary embodiments illustrated in the appended drawings.

Figure 2:
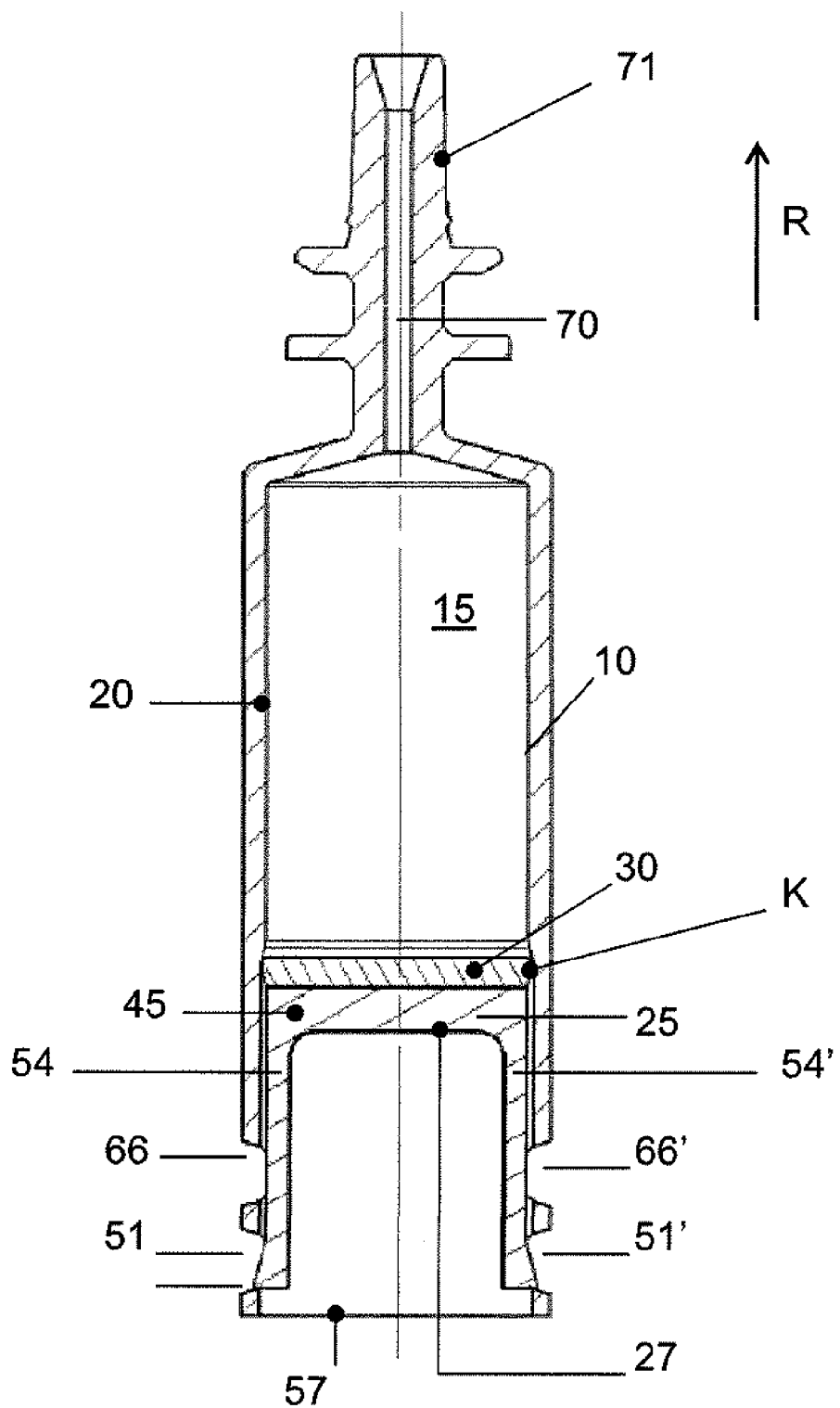
FIG. 2 depicts a longitudinal cross section of the ampoule of FIG. 1, with the sealing element in the first compression state.

Referring to FIGS. 1 and 2, an ampoule according to at least one embodiment described herein is schematically depicted. The cylindrical ampoule body 10 is a thermoplastic material which is injection-molded to form an interior space 15 in which a flowable substance such as insulin or another medicinal substance, may be received. The piston 25 is a two-component injection-molded part comprising a thermoplastic basic body 45 and a sealing element 30 which is placed onto the basic body 45. The piston 25 is positioned in the ampoule body 10 such that the sealing element 30 is in contact with the inner circumferential surface 20 of the ampoule in a contact zone K. That end surface of the basic body 45 which points towards the opening 57 of the ampoule body 10 is designed as a plane surface 27 by which a compressive force can be transmitted to the piston 25, thus resulting in displacement of the piston in a direction of displacement R. The direction of displacement R corresponds to the longitudinal axis of the ampoule.

Figure 3:
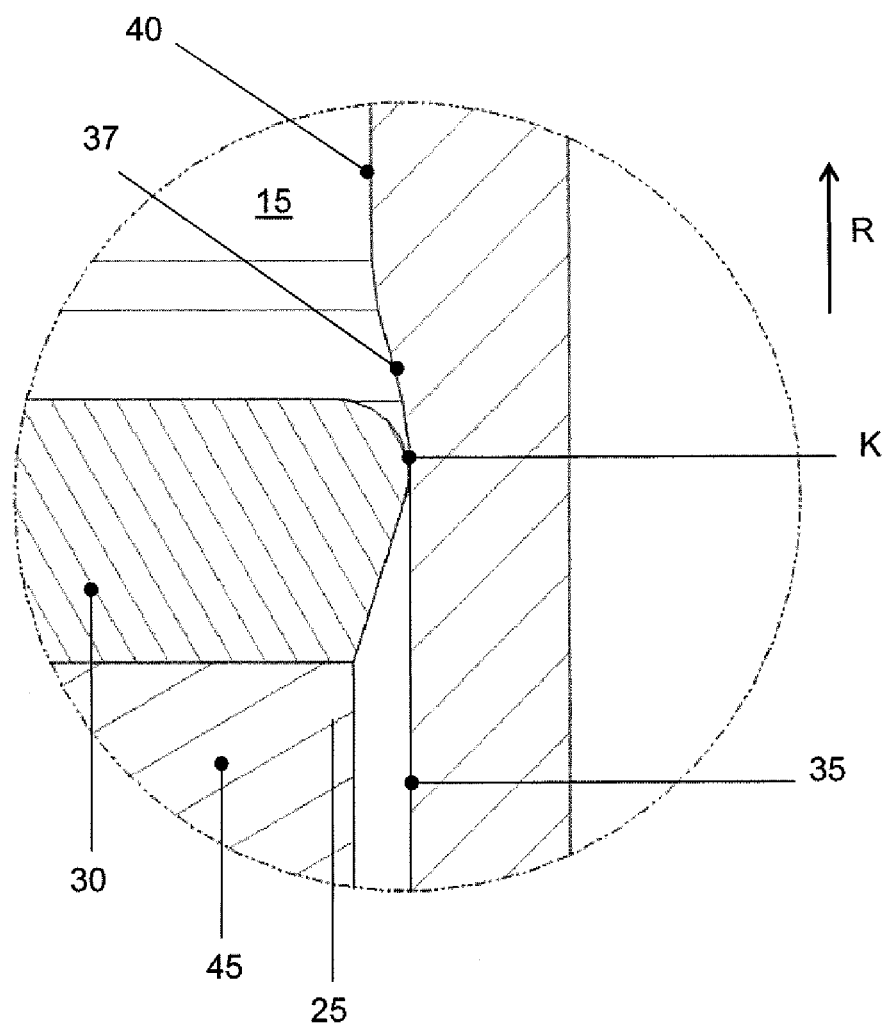
FIG. 3 depicts a magnified view of a detail of the contact zone between a sealing element and an inner circumferential surface of the longitudinal cross section depicted in FIG. 2.
Figure 4:
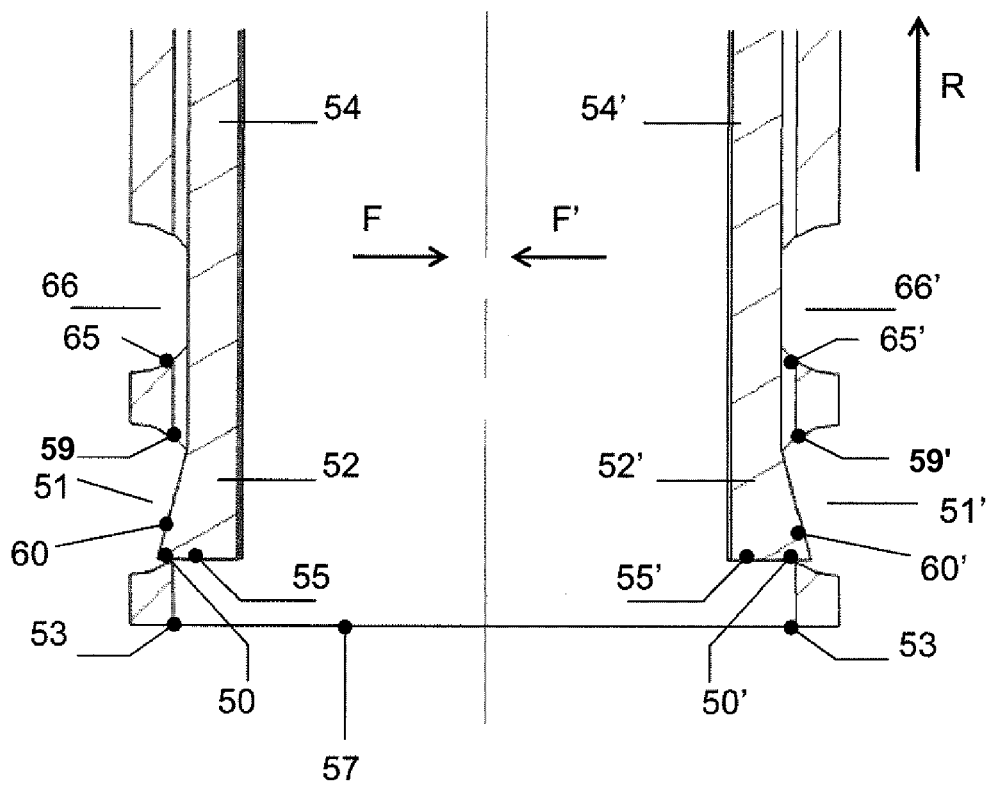
FIG. 4 depicts a magnified view of a detail of a first and second blocking device of the longitudinal cross section depicted in FIG. 2.

Referring to FIGS. 2-4, the sealing element 30 makes contact with the inner circumferential surface 20 of the ampoule body 10 in the guide region 35. FIG. 3 shows the transition between guide region 35 and sealing region 40. In order to prevent removal of the piston 25 from the ampoule body 10, a first blocking device, which is illustrated in FIG. 4, is provided. For this purpose, the ampoule body 10 has, on its circumference, first cutouts 51, 51', the edges of which face the opening 57 of the ampoule body forming first ampoule-body-side stops 50, 50'. The piston 25 has radially resilient spring arms 54, 54' which protrude perpendicularly from it and end in catches 52, 52'. The catches 52, 52' each comprise a piston-side stop 55, 55' and a sliding surface 60, 60'. During assembly, the piston 25 is introduced from the opening 57 into the ampoule body 10 in the direction of displacement R. In the process, the spring arms 54, 54' spring out of their relaxed inoperative position in the spring direction F, F' radially outwards towards the ampoule axis and the sliding surfaces 60, 60' slide over the edge 53 of the inner circumferential surface of the ampoule body. As soon as the catches 52, 52' enter the first cutouts 51, 51' during further displacement of the piston 25 in the direction of displacement R, the catches 52 move opposite the spring direction F, F' into a relaxed position such that they project into the first ampoule-body-side cutouts 51, 51'. When the piston 25 is moved opposite the direction of displacement R, the piston-side stops 55, 55' engage the first ampoule-body-side stops 50, 50', and prevent further movement of the piston 25 in the direction of the opening 57. In contrast, displacement of the piston 25 in the direction of displacement R remains possible as the sliding surfaces 60, 60' contact the edges 59, 59' of the first cutouts 51 which lie opposite the first ampoule-body-side stops 50, 50' and, in the process, displace the spring arms 54, 54' in the spring direction F, F'.

Figure 5:
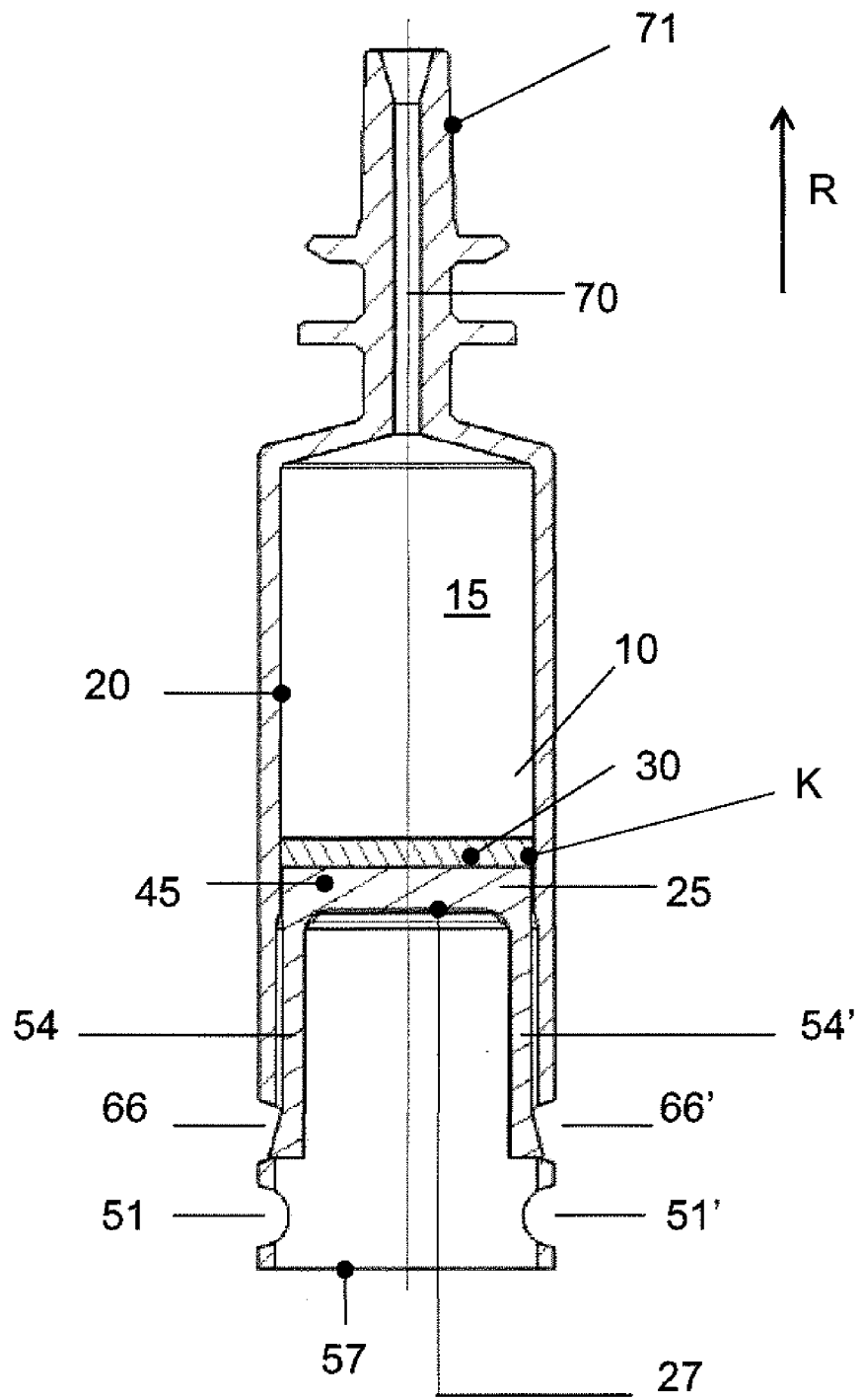
FIG. 5 depicts a longitudinal cross section of an ampoule according to FIG. 1, with the sealing element in the second compression state.

Further movement of the piston 25 in the direction of displacement R moves the contact zone K from the guide region 35 into the sealing region 40 where the interior space 15 of the ampoule body 10 has a smaller interior diameter. In this position, the sealing element 30 is in a second compression state as shown in FIG. 5. In order to prevent jamming or even possible damage to the sealing element 30 when the contact zone K is displaced from the guide region 35 into the sealing region 40, the two regions are connected by a continuous transition region 37. In the case of a cylindrical ampoule cross section, the inner circumferential surface 20 of the ampoule body 10 in the transition region 37 is a cylindrical truncated cone, the diameter of which tapers from the inside diameter of the interior space 15 of the ampoule in the guide region 35 to the inside diameter of the interior space 15 of the ampoule in the sealing region 40. In other embodiments the ampoule may be formed with a contour which smoothly connects (i.e., a transition without defined edges) the guide region 35, to the sealing region 40, in the transition region 37. A displacement of the contact zone K opposite the direction of travel R out of the sealing region 40 into the guide region 35 results in a loss of the seal between the inside diameter of the interior space and the ampoule and should be prevented. Accordingly, a second blocking device, the operation of which is analogous to the first blocking device, is provided with second cutouts 66, 66' and second ampoule-body-side stops 65, 65'. The second cutouts 66, 66' are offset in relation to the first cutout 51, 51' in the direction of displacement R. The spring arms 54, 54' with catches 52, 52' work in conjunction with the first blocking device and the second blocking device, and therefore the operation of the piston-side stops 55, 55' and the sliding surfaces 60, 60' for both blocking devices is similar.

Alternatively, other constructions may be possible for the blocking devices. For example, the inner circumferential surface 20 of the ampoule body 10 may be formed with two pairs of catches which are offset with respect to each other in the direction of displacement R while corresponding cutouts are respectively formed in the radially resilient spring arms 54, 54'.

Further movement of the piston in the direction of displacement R causes the catches 52, 52' to press resiliently against the inner circumferential surface 20 of the ampoule body 10 due to the spring force of the spring arms 54, 54'. In addition to the friction between sealing element 30 and inner circumferential surface 20 in the second compression state of the sealing element 30, this interaction between the catches 52, 52' of the spring arms 54, 54' and the inner circumferential surface 20 of the ampoule body 10 constitutes protection against inadvertent displacement of the piston 25 in the interior space 15 of the ampoule body 10. Specifically, displacement of the piston 25 results in a sliding frictional force between the inner circumferential surface 20 and the catches 52, 52' in a direction opposite the displacement. At the same time, the contact between the inner circumferential surface 20 and the catches 52, 52' prevents the piston 25 from tilting in the ampoule body 10. Accordingly, the catches 52, 52' act as guide elements for the piston as they press resiliently against the inner circumferential surface 20 of the ampoule body 10.

To ensure a symmetrical introduction of force into the piston 25, the first blocking device and the second blocking device are each present in duplicate and are offset by 180° with respect to each other on the circumference of the ampoule. Alternatively, the first and second blocking devices may be present in triplicate and offset by 120° or another angular orientation other than 180°.

The interior space 15 of the ampoule body is fluidly coupled to an outlet opening 70 which is provided with an end surface 71 for coupling to a conventional cannula or to a catheter such as a Luer cone.

Figure 6:
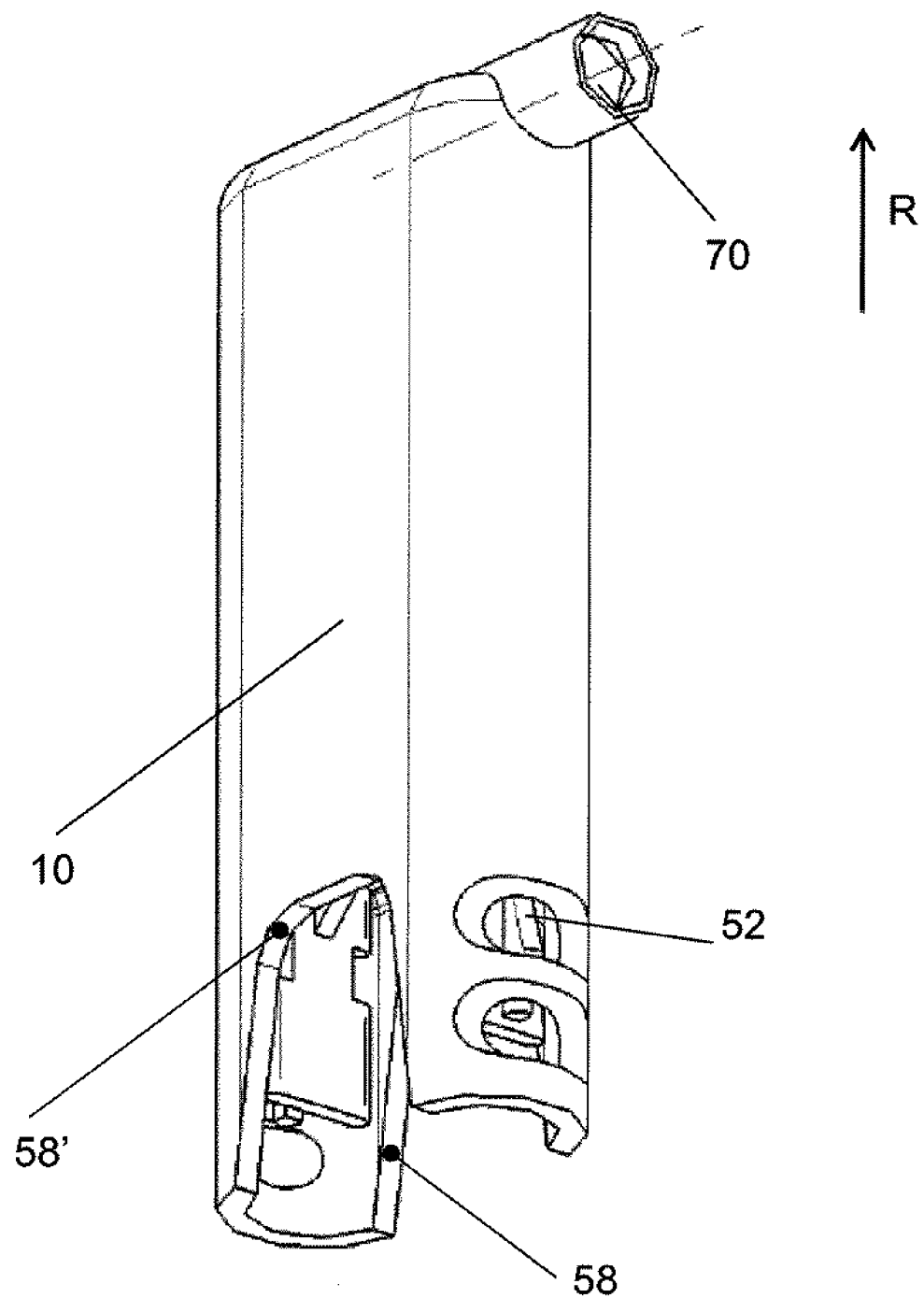
FIG. 6 depicts an isometric view of an ampoule according to one or more embodiments shown and described herein.
Figure 7:
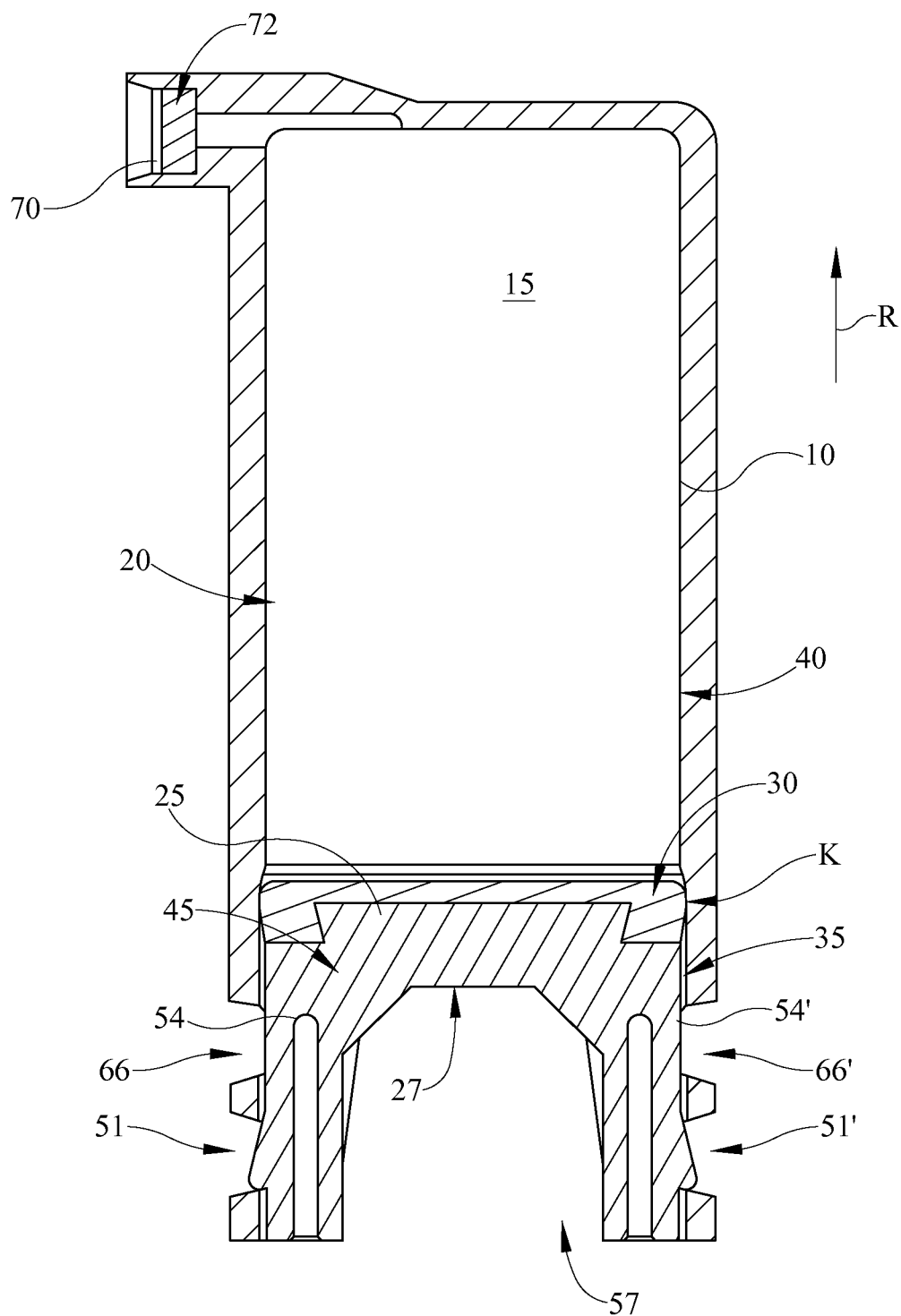
FIG. 7 depicts a longitudinal cross section of an ampoule according to FIG. 6, with the sealing element in the first compression state.
Figure 8:
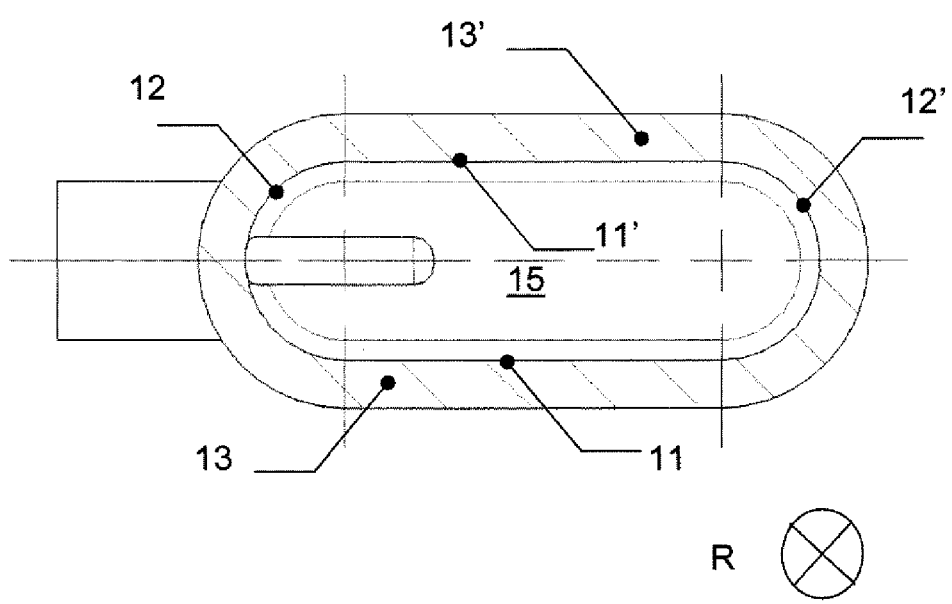
FIG. 8 depicts a radial cross section of the ampoule body in the sealing region of an ampoule according to FIG. 6.

Referring now to FIGS. 6-8, a second embodiment of an ampoule is schematically depicted. Specifically, FIG. 7 shows a longitudinal section of the ampoule of FIG. 6 with the sealing element 30 in the first compression state while FIG. 8 shows a radial cross section of the ampoule body 10 in the sealing region 40. This embodiment differs from the embodiment illustrated in FIGS. 1 to 5 in the cross sectional shape of the ampoule body 10. Specifically, the interior space 15 of the ampoule body 10 is defined by two plane-parallel surfaces 11, 11' and two cylindrical circumferential surfaces 12, 12' connecting the surfaces 11, 11'. This results in a flatter profile compared to a cylindrical ampoule, which is advantageous in particular for use in injection or infusion systems. Furthermore, in this embodiment, the outlet opening 70 is arranged transversely with respect to the direction of displacement R, which leads to a smaller axial dimension compared to an axial arrangement of the outlet opening. A fluidically tight septum 72 which can be pierced with a hollow cannula is located in the outlet opening.

Referring collectively to FIGS. 6-8, starting from the opening 57, the plane-parallel walls 13, 13' (FIG. 8) have U-shaped cutouts 58, 58' (FIG. 6) in the guide region 35 (FIG. 7). Referring now to FIG. 7, these facilitate grasping the piston 25 or a drawing-up device and may be releasably connected to the piston 25 such that the piston can be displaced in a direction opposite the direction of displacement R. This is required if liquid is to be guided through the outlet opening 70 by means of the piston 25 being pulled back opposite the direction of displacement R.

Figure 9:
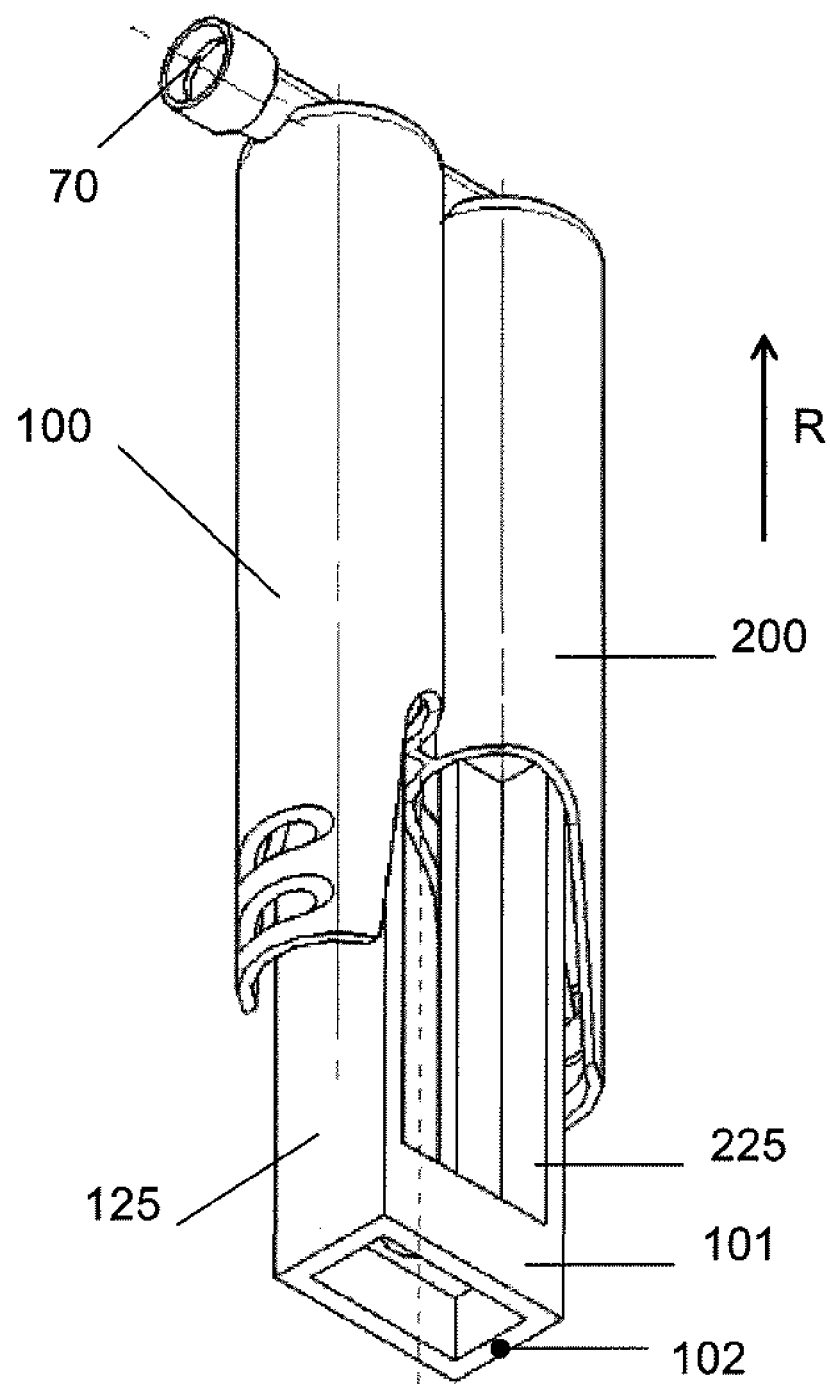
FIG. 9 depicts an isometric view of an ampoule comprising a first partial ampoule and a second partial ampoule according to one or more embodiments shown and described herein.
Figure 10:
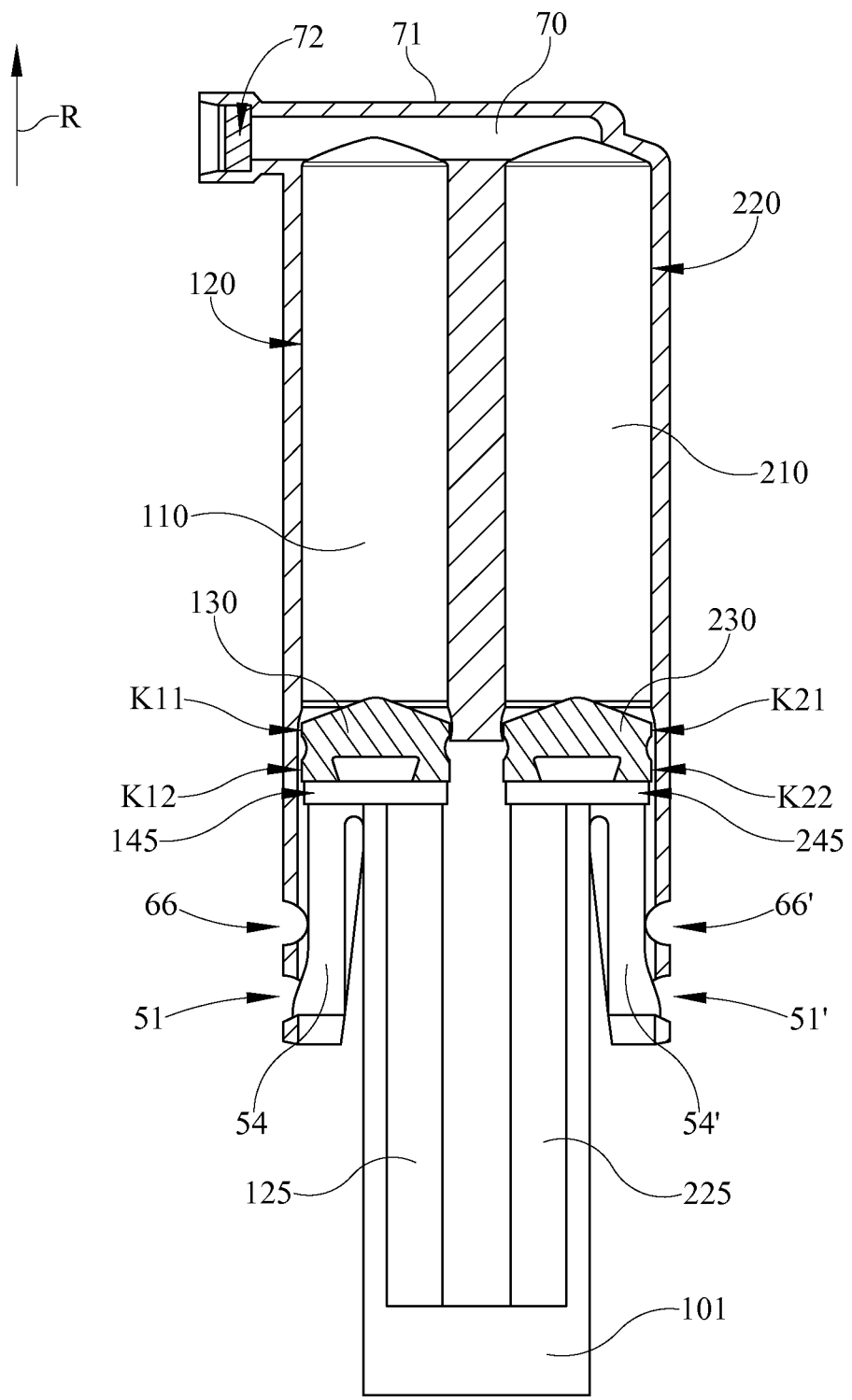
FIG. 10 depicts a longitudinal cross section of an ampoule according to FIG. 9, with the sealing elements of the partial ampoules in the first compression state.
Figure 11:
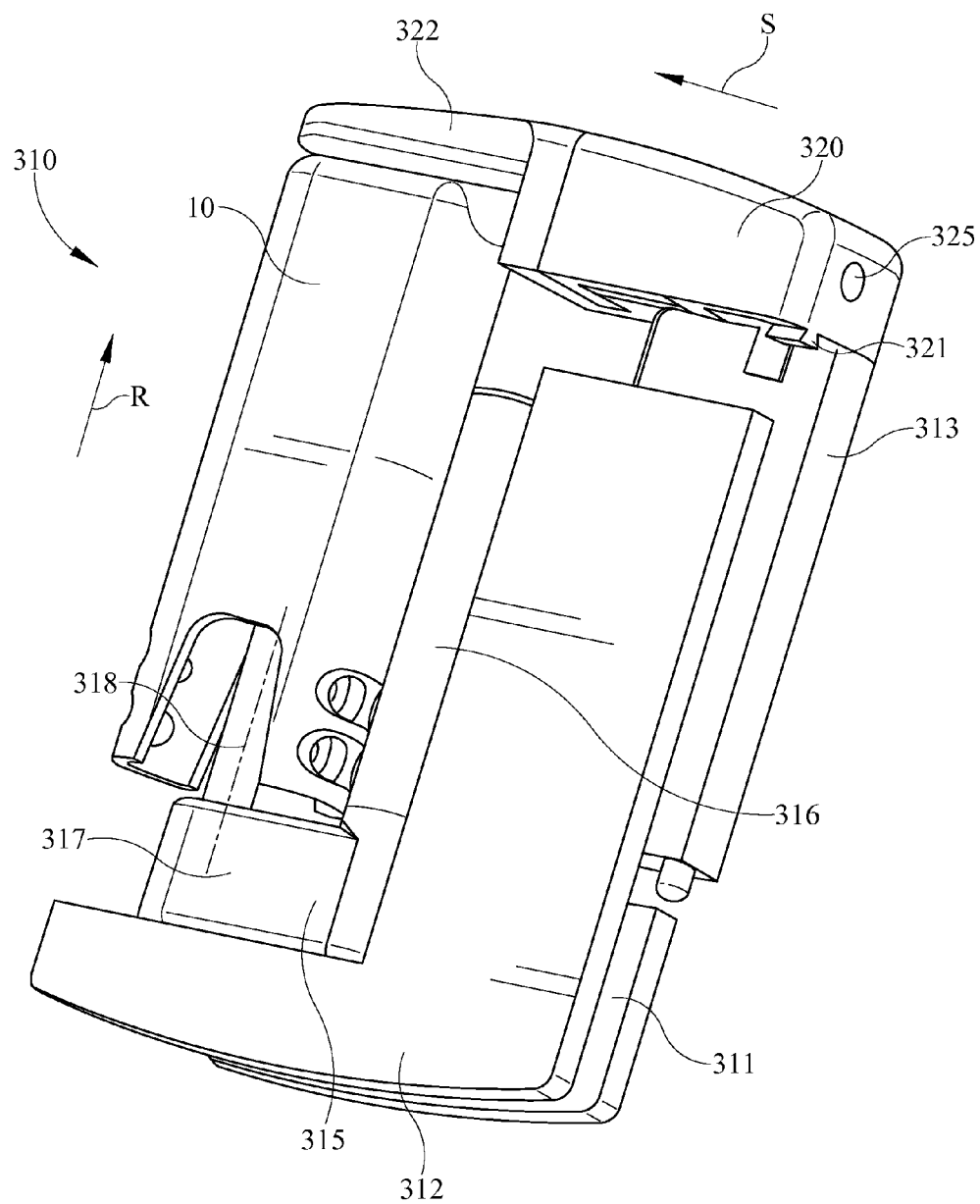
FIG. 11 depicts an isometric view of a metering system with an ampoule corresponding to FIGS. 6-8.

Referring to FIGS. 9 and 10, another embodiment of an ampoule is schematically depicted. Specifically, FIG. 9 shows an ampoule which comprises a first partial ampoule 100 and a second partial ampoule 200 while FIG. 10 shows a longitudinal cross section of the ampoule of FIG. 9.

An ampoule corresponding to this embodiment comprises two individual partial ampoules 100 and 200. The partial ampoules 100, 200 are constructed according to the single ampoule embodiments shown and described herein, with the partial ampoules 100 and 200 being arranged parallel to each other and being connected via a web such that they have a common direction of displacement R. In one embodiment, the piston 125 of the first partial ampoule is coupled to the piston 225 of the second partial ampoule via a connecting piece 101 in such a manner that a displacement in the common direction of displacement R or opposite the common direction of displacement R takes place jointly for piston 125 and piston 225. The end surface 102 of the connecting piece 101 can serve at the same time for the transmission of a compressive force to the pistons 125, 225, resulting in a displacement of piston 125 and piston 225 in the direction of the displacement R.

In order to improve guidance of the piston in the ampoule(s), the sealing element 130 is configured in such a manner that it has two contact zones K11 and K12, which are offset with respect to each other, with the inner circumferential surface 120 of the first ampoule body 110 in the direction of displacement R, and the sealing element 230 is configured in such a manner that it has two contact zones K21 and K22, which are offset with respect to each other, with the inner circumferential surface 220 of the second ampoule body 210 in the direction of displacement R. The ampoule body 110 and the ampoule body 210 have a common outlet opening 70 which is transversely oriented with respect to the direction of displacement R. A fluidically tight septum 72 which can be pierced with a hollow cannula is located in the common outlet opening 70.

In this embodiment, the sealing elements 130 and 230 together with the basic bodies 145 and 245 of the pistons 125 and 225 and the connecting piece 101 are designed as an integral two-component injection-molded part.

The operation of the first blocking device and the second blocking device in FIGS. 9 and 10 generally correspond to the embodiments of the ampoule shown and described in FIGS. 1-8.

The basic bodies 145 and 245 work together with the connecting piece 101 as a drawing-up device for displacement of the pistons 125 and 225 opposite the direction of displacement R.

Referring to FIGS. 6-8 and 11, FIG. 11 shows a metering system for medicaments such as insulin. The metering system comprises an ampoule body 10 corresponding to the ampoule shown in FIG. 8, and an infusion system 310 which entirely or partially accommodates the ampoule body 10. The infusion system comprises an advancing unit 315 in the form of a spindle drive with a DC motor or stepping motor 316, a reduction and deflection gearing 317 and a piston rod 318. The piston rod 318 can be extended in a controlled manner out of the reduction and deflection gearing 317 in the direction of displacement R in order to empty out a medicament contained in ampoule and, in the process, exert a compressive force by means of a pressure plate (not illustrated) on the plane surface 27 of the piston 25, this resulting in a controlled displacement of the piston 25 in the direction of displacement R. Furthermore, the infusion device 310 comprises an electronic controller 311, a user interface 312 and a power supply 313. The user interface can comprise an alphanumeric display (not illustrated) for providing information to the user, and also one or more keying elements (not illustrated) by which a user may input information into the infusion device 310.

An adapter 320 fluidically couples the outlet opening 70 of the ampoule to an injection or infusion cannula (not illustrated). The adapter 320 furthermore comprises an extension arm 322 which projects over the end surface 71 of the ampoule body 10 and thus forms a stop for the ampoule body 10, the stop fixing the ampoule in the direction of displacement R and constituting a counter-bearing for the controlled displacement of the piston 25 by the advancing unit 315.

The components of the metering system are assembled as follows: (1) The ampoule body 10 which is filled with insulin is inserted into the infusion device 310 counter to the direction of displacement R. (2) The adapter 320 is releasably coupled to the infusion device 310 by displacement of the adapter in the direction S which is transverse to the direction of displacement R. To guide the adapter 320, the adapter is fitted with a dovetail 321 which is fastened to the adapter 320. The dovetail 321 corresponds to a groove (not illustrated) on the infusion device 310. The ampoule body 10 is also fluidly coupled to the adapter 320 by the same movement in the direction S. To facilitate fluid coupling, the adapter 320 comprises a hollow cannula (not visible in FIG. 11), the longitudinal axis of which corresponds to the direction S. The hollow cannula of the adapter 320 pierces the septum 72 arranged in the outlet opening 70. The outlet opening 325 of the adapter 320 may be fluidly coupled to an infusion catheter which is integral with the adapter, or may be fluidly coupled to an infusion catheter with a fluidic coupling. As an alternative, the outlet opening 325 can be fluidly coupled to an infusion cannula which is integral with the adapter or connected to the adapter via a fluidic coupling.

Furthermore, the adapter 320 can comprise a monitoring device for monitoring the metering, such as a pressure or flow sensor, or the adapter can contain a flexible pressure transmission membrane which transmits the fluidic pressure to a pressure sensor located in the infusion device 310.

What is claimed is:

1. An ampoule for a flowable substance comprising:
    an ampoule body comprising an interior space for receiving the flowable substance and an inner circumferential surface having a guide region and a sealing region, wherein the guide region and the sealing region are positioned along a longitudinal axis of the ampoule body and the cross-sectional area of the ampoule body in the sealing region is less than the cross-sectional area of the ampoule body in the guide region;
    a piston disposed in the interior space of the ampoule body such that the piston is slidably displaceable along the longitudinal axis of the ampoule body in a direction of displacement, the piston comprising at least one sealing element for forming a seal with the inner circumferential surface of the ampoule body in a contact zone on an outer circumference of the at least one sealing element; and
    a blocking device which prevents movement of the contact zone from the sealing region to the guide region, wherein:
        the blocking device comprises an ampoule-body-side stop, a piston-side stop and a sliding surface.

2. The ampoule according to claim 1, wherein the piston is a two component injection-moulded part comprising a basic body and the at least one sealing element, wherein the basic body is formed from a thermoplastic material and the at least one sealing element is formed from a thermoplastic elastomer.

3. The ampoule according to claim 1, wherein the inner circumferential surface has a transition region disposed between the guide region and the sealing region.

4. The ampoule according to claim 1, wherein the ampoule body has at least one outlet opening.

5. The ampoule according to claim 1, wherein the at least one sealing element comprises at least two contact zones.

6. The ampoule according to claim 1, wherein the piston comprises a guide element which is offset from the at least one sealing element in a direction of an opening of the ampoule body, wherein the guide element makes contact with the inner circumferential surface of the ampoule body.

7. The ampoule according to claim 1, wherein the piston comprises a coupling device for coupling the piston to an advancing drive of an injection or infusion device.

8. The ampoule according to claim 1, wherein the at least one sealing element and the inner circumferential surface of the ampoule body do not seal with regard to a medium with a sterilizing effect when the contact zone is in the guide region of the inner circumferential surface.

9. The ampoule according to claim 1, wherein the ampoule comprises a drawing-up device for displacing the piston in a direction opposite the direction of displacement.

10. The ampoule according to claim 1, wherein the ampoule comprises an additional blocking device which prevents removal of the piston from the ampoule body in a direction opposite the direction of displacement.

11. The ampoule according to claim 10, wherein the additional blocking device comprises an additional ampoule-body-side stop, a piston-side stop and a sliding surface.

12. The ampoule according to claim 11, wherein the sliding surface of the additional blocking device is the sliding surface of the blocking device.

13. The ampoule according to claim 11, wherein the piston-side stop of the additional blocking device is the piston-side stop of the blocking device.

14. The ampoule according to claim 13, wherein the sliding surface of the additional blocking device is the sliding surface of the blocking device.

15. The ampoule according to claim 14, wherein:
the piston comprises at least one radially resilient spring arm extending from the piston towards an opening of the ampoule body, the at least one radially resilient spring arm having a catch forming the piston-side stop and the sliding surface; and
the ampoule body has a first cutout and a second cutout offset from the first cutout in the direction of displacement, wherein the additional ampoule-body-side stop is formed by a wall of the first cutout, the ampoule body-side stop is formed by a wall of the second cutout, and the catch projects into the first cutout and into the second cutout when the at least one radially resilient spring arm is in an unloaded state.

16. The ampoule according to claim 15, wherein the catch presses against the inner circumferential surface of the ampoule body when the at least one radially resilient spring arm is deformed by the inner circumferential surface of the ampoule body.

17. A metering system for a flowable substance comprising an injection or diffusion device for dispensing the flowable substance from an ampoule having an ampoule body, a piston and a blocking device, wherein:
the ampoule body comprises an interior space for receiving the flowable substance and an inner circumferential surface having a guide region and a sealing region, wherein the guide region and the sealing region are positioned along a longitudinal axis of the ampoule body and the inner circumferential surface tapers in from the guide region to the sealing region;
the piston is disposed in the interior space of the ampoule body such that the piston is slidably displaceable along a longitudinal axis of the ampoule body in a direction of displacement, the piston comprising at least one sealing element for forming a seal with the inner circumferential surface of the ampoule body in a contact zone on an outer circumference of the at least one sealing element, wherein:
the blocking device prevents movement of the contact zone from the sealing region to the guide region and comprises an ampoule-body-side stop, a piston-side stop and a sliding surface; and
the injection or diffusion device is connectable to the piston of the ampoule to advance the piston in the interior space in the direction of displacement such that the flowable substance is dispensed from the ampoule.

* * * * *